(12) United States Patent
Matsumoto et al.

(10) Patent No.: US 7,955,859 B2
(45) Date of Patent: Jun. 7, 2011

(54) FLUORESCENT LABELING COMPOUND

(75) Inventors: Kazuko Matsumoto, Tokyo (JP); Nishioka Takuya, Tokyo (JP); Miyabe Masahito, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 566 days.

(21) Appl. No.: 11/991,101

(22) PCT Filed: Aug. 31, 2006

(86) PCT No.: PCT/JP2006/317189
§ 371 (c)(1),
(2), (4) Date: Feb. 27, 2008

(87) PCT Pub. No.: WO2007/026808
PCT Pub. Date: Mar. 8, 2007

(65) Prior Publication Data
US 2009/0136931 A1  May 28, 2009

(30) Foreign Application Priority Data

Aug. 31, 2005 (JP) ................. 2005-251834

(51) Int. Cl.
*G01N 21/76* (2006.01)
*C07D 487/00* (2006.01)

(52) U.S. Cl. ....................... 436/172; 540/471

(58) Field of Classification Search .................. 424/9.6, 424/9.61
See application file for complete search history.

(56) References Cited

U.S. PATENT DOCUMENTS

| | | | | |
|---|---|---|---|---|
| 4,637,988 A | * | 1/1987 | Hinshaw et al. | 436/546 |
| 5,571,897 A | | 11/1996 | Takalo et al. | |
| 6,340,744 B1 | * | 1/2002 | Leif et al. | 534/15 |
| 2005/0255465 A1 | | 11/2005 | Matsumoto et al. | |

FOREIGN PATENT DOCUMENTS

| | | |
|---|---|---|
| JP | 2001-335574 | 12/2001 |
| WO | WO-93/11433 | 6/1993 |
| WO | WO-03/076938 | 9/2003 |

* cited by examiner

*Primary Examiner* — Noble Jarrell
(74) *Attorney, Agent, or Firm* — Peter F. Corless; Christine C. O'Day; Edwards Angell Palmer & Dodge LLP

(57) ABSTRACT

A rare-earth fluorescent complex which forms a fluorescent complex with two or more rare-earth metals such as europium and terbium and can effectively be excited at a wavelength of 340 nm or longer; a fluorescent labeling agent comprising the rare-earth fluorescent complex; a method of fluorescent labeling in which the rare-earth fluorescent complex is used as a labeling agent; and a method of fluorometric analysis in which the fluorescent labeling agent is used. The rare-earth fluorescent complex is characterized by having a cyclic ligand comprising a 4-biphenyl-2,2':6',2"-terpyridine skeleton and a 2,6-bis(3'-aminomethyl-1'-pyrazolyl)pyrazine skeleton bonded thereto.

21 Claims, 4 Drawing Sheets

# FLUORESCENT LABELING COMPOUND

TECHNICAL FIELD

The present invention relates to a rare-earth metal fluorescent complex which forms fluorescent complex with 2 or more rare-earth metals such as europium and terbium and can effectively be excited at a wavelength of 340 nm or longer. In more detail, the present invention relates to the rare-earth fluorescent complex characterized by having a cyclic ligand comprising a 4-biphenyl-2,2':6',2"-terpyridine skeleton and a 2,6-bis-(3'-aminomethyl-1'-pyrazolyl)-pyrazine skeleton bonded thereto; a fluorescent labeling agent comprising said rare-earth metal complex, a method of fluorescence labeling wherein the rare-earth metal complex is used as a labeling agent; a method of fluorometric analysis wherein the fluorescent labeling agent is used; and a reagent for the fluorometric analysis.

BACKGROUND ART

An immunoassay using an antigen-antibody reaction, a DNA hybridization assay or the like has conventionally been used for microanalysis of biological samples. In such analyses, an antibody or DNA is required to be labeled with the labeling agents. The labeling agents generally used are those modified with fluorescence, radioisotope or enzyme, which enable highly sensitive detection.

Radioisotope labeling, although highly sensitive, has some disadvantages involving risks in storage, use and disposal. Enzyme labeling also has some defects. Because of a high molecular weight of an enzyme, the labeling stability and reproducibility may often be impaired by the external factors such as temperature. The activities of both enzyme and the labeled substance may often be reduced due to the bindings of the enzyme labeling agent to the substance to be labeled.

As fluorescent labeling methods, the labeling with organic fluorescent dye such as fluorescein, rhodamine and dansyl chloride has been known. However, it has a defect in that the fluorescence detection is likely to be disturbed to a large extent by the background noises due to the scattered excitation light and the fluorescence response derived from other coexisting substances within a sample, whereby making a highly sensitive measurement difficult.

The labeling with a rare-earth fluorescent complex has also been known as one of the fluorescent labeling methods. The rare-earth fluorescent complex has a long fluorescence lifetime (of from several tens to several hundreds of microseconds or longer compared with a common organic fluorescent substance of which fluorescent lifetime is several nanoseconds), a large Stokes shift and a sharp fluorescent peak, which enables the highly sensitive fluorescence measurement if used for a time-resolved fluorescence assay, by eliminating a short-life background noises derived from an excitation light or other coexisting substances. The time-resolved fluorescence assay with the use of the rare-earth fluorescent complex of the above described characteristics as a labeling agent has already been developed.

The 2,2':6',2"-terpyridine derivative has been reported as one of the rare-earth fluorescent complexes (See Patent Reference 1). The 2,2':6',2"-terpyridine derivative directed to form a complex with a radioactive metal in use for a radioactive reagent has also been reported (See Patent Reference 2).

Meanwhile, the present inventors have already developed chlorosulfonyl quadridentate beta-diketone labeling agents that can directly label a protein having an amino group and have investigated an application thereof to a time-resolved fluorescence assay (See Patent References 3 and 4). However, said labeling agent of a chlorosulfonylated tetradentate β-diketone type generally had a defect of poor solubility in water, whereby reduced the solubility of the labeled biomaterials and resulted in precipitation from the solution, particularly when the labeled biomaterials were small (for example, a nucleic-acid base of a low molecular weight having amino groups, and other organic compounds). The buffers usable were limited due to the insufficient chelating ability thereof, which was another defect.

The present inventors have developed a large number of labeling agents of rare-earth fluorescent complexes and studied the application thereof to the time-resolved fluorescence assay. The already developed N,N,N',N'-{2,6-bis-(3'-aminomethyl-1'-pyrazolyl)-4-phenyl pyridine}-tetra-acetic acid (hereinafter abbreviated to as BPTA) was able to form a complex with terbium and europium and emit strong fluorescence but had a maximum excitation wavelength at 320 nm which was short. On the other hand, (2,2',2",2"'-{4'-{[(4,6-dichloro-1,3,5-triazine-2-yl)-amino]-biphenyl-4-yl}-2,2': 6'2"-terpyridine-6,6"-di-yl)-bis-(methylene nitro)tetra acetic acid} (hereinafter abbreviated to as DTBTA) was able to be excited at 340 nm or longer, but was able to form a fluorescent complex only with europium (See Patent Reference 5).

It is important for the fluorescent labeling agent to have the longer excitation wavelength in order to overcome instrumental limitation involved in optical elements such as a lens and a light source as well as minimize the effect to the samples, therefore the development of a rare-earth fluorescent complex with excitation wavelength of 340 nm or longer has been desired.

DNA probe method has widely been employed in DNA analysis. Both a standard sample and a test sample (analyte) labeled with two or more labeling agents are furnished to the same probe DNA, followed by quantitatively determines the amount of DNA in a test sample based on the results of competitive hybridization. For the method like this, the construction of a fluorescence emitting complex with a plurality of rare-earth ions is desired.

Patent Reference 1: JP3-500297/1991, A
Patent Reference 2: JP7-506667/1995, A
Patent Reference 3: JP9-241233/1997, A
Patent Reference 4: JP2000-111480, A
Patent Reference 5: WO2003/076938

PROBLEM TO BE SOLVED BY THE INVENTION

The present invention has been made in view of the current status described above, aiming at providing a rare-earth fluorescent complex formed with 2 or more rare-earth metals such as europium and terbium that can effectively be excited at a wavelength of 340 nm or longer; a fluorescent labeling agent comprising said rare-earth fluorescent complex; a florescent labeling method using said rare-earth fluorescent complex as a labeling agent; a method of fluorometric analysis using said fluorescent labeling agent; and the like.

Moreover, the present invention is to provide a novel labeling reagent which has a binding group capable of binding to a substance to be labeled (e.g., a biomaterial, a physiologically active substance, etc.) and easily forms a complex with a plurality of rare-earth ions, wherein the resulting complex is stable enough in an aqueous solution, has a sufficient fluorescent intensity and a long fluorescent lifetime regardless of the types of buffer. The present invention is further to provide a complex comprising said labeling reagent and rare-earth metal ions, a fluorescent labeling agent comprising said complex, a method of fluorometric analysis using said fluorescent labeling agent, and the like.

MEANS FOR SOLVING THE PROBLEMS

The present inventors have conducted a extensive study to solve the above described problems and finally found that a cyclic ligand comprising in its structure 4-biphenyl-2,2':6', 2"-terpyridine and N,N,N',N'-{2,6-bis-(3'-aminomethyl-1'-pyrazolyl)-pyrazine is capable of forming a fluorescent complex with either terbium or europium, and the resulting complex can effectively be excited at the wavelength of 340 nm or longer; thereby completed the present invention.

The present invention relates to a rare-earth fluorescent complex having a ligand for the formation of a rare-earth fluorescent complex which can form a complex with 2 or more of rare-earth metals; the complex can emit fluorescence and can effectively be excited at a wavelength of 340 nm or longer. In more detail, the present invention relates to the rare-earth fluorescent complex having a cyclic ligand comprising a 4-biphenyl-2,2':6',2"-terpyridine skeleton and a 2,6-bis-(3'-aminomethyl-1'-pyrazolyl)-pyrazine skeleton. Further, the present invention relates to a rare-earth fluorescent complex of the following general formula (II):

(II)

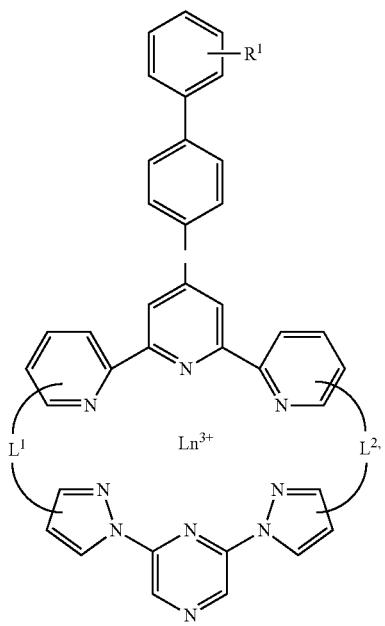

wherein:

$R^1$ is a nitro group or an optionally substituted amino group;

$L^1$ and $L^2$ each independently is a straight or branched chain $C_1$-$C_6$ alkylene group with at least one carbon atom optionally substituted with a nitrogen atom, each of which links both rings and optionally comprises an anionic group to neutralize positive charges of rare-earth ions; and Ln represents a rare-earth metal.

In more detail, the present invention relates to a rare-earth fluorescent complex of the following general formula (III):

(III)

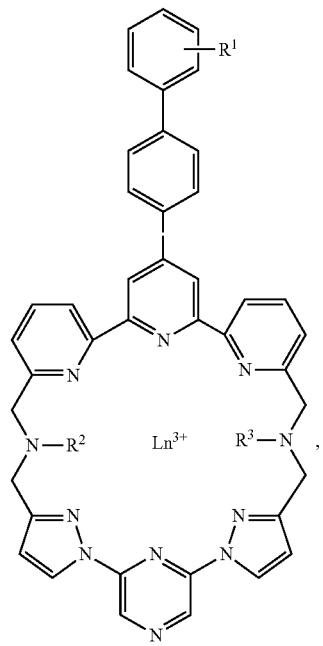

wherein:

$R^1$ is a nitro group or an optionally substituted amino group;
$R^2$ and $R^3$ each independently is a carboxyalkyl group; and
Ln represents a rare-earth metal.

Moreover, the present invention relates to a fluorescent labeling agent to label a substance to be labeled, comprising the rare-earth fluorescent complex of the present invention; a florescent labeling method using said fluorescent labeling agent; a biomaterial or a physiologically active substance labeled with said fluorescent labeling agent; a fluorescence assay for the measurement of fluorescence in the substances labeled with said fluorescent labeling agent; and a kit for the fluorescence assay comprising the said fluorescent labeling agent.

The present invention further relates to a compound of the following general formula (I) or a salt thereof.

(I)

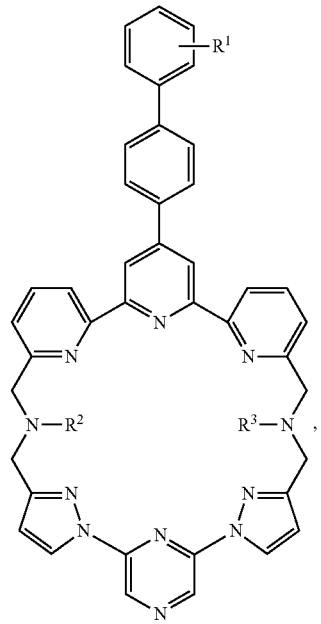

wherein:

R¹ is a nitro group or an optionally substituted amino group;

R² and R³ each independently is a carboxyalkyl group.

In one embodiment, the present invention relates to a terbium complex having a ligand, which can form a complex with terbium; the resulting complex can emit fluorescent light and excitable at a wavelength of 340 nm or longer.

The present invention is explained in more detail as follows:

(1) A compound represented by the following general formula (I) or a salt thereof.

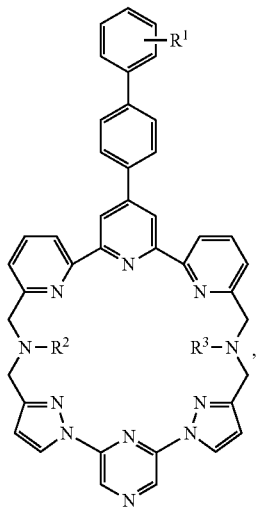

(I)

wherein:

R¹ is a nitro group or an optionally substituted amino group;

R² and R³ each independently is a carboxyalkyl group.

(2) The compound or the salt thereof according to (1), wherein each R² and R³ of the general formula (I) is a carboxymethyl group.

(3) The compound or the salt thereof according to (1) or (2), wherein the substituent of amino group in R¹ of the general formula (I) is a binding group that binds to a substance to be labeled.

(4) A rare-earth fluorescent complex having a ligand for the formation of the rare-earth fluorescent complex which can form a complex with 2 or more rare-earth metals, the complex can emit fluorescent light, and is excitable at a wavelength of 340 nm or longer.

(5) A rare-earth fluorescent complex, wherein 4-biphenyl-2,2':6',2''-terpyridine skeleton and 2,6-bis(3'-aminomethyl-1'-pyrazolyl)pyrazine skeleton are bonded to form a cyclic ligand.

(6) A rare-earth fluorescent complex is a compound represented by the following general formula (II):

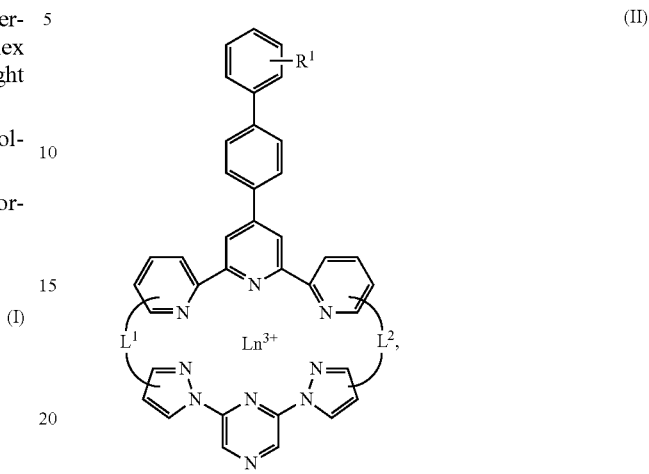

(II)

wherein:

R¹ is a nitro group or an optionally substituted amino group;

L¹ and L² each independently is a straight or branched chain C₁-C₆ alkylene group with at least one carbon atom optionally substituted with a nitrogen atom, each of which links both rings and optionally comprises an anionic group to neutralize positive charges of rare-earth ions; and Ln represents a rare-earth metal.

(7) A rare-earth fluorescent complex represented by the following general formula (III):

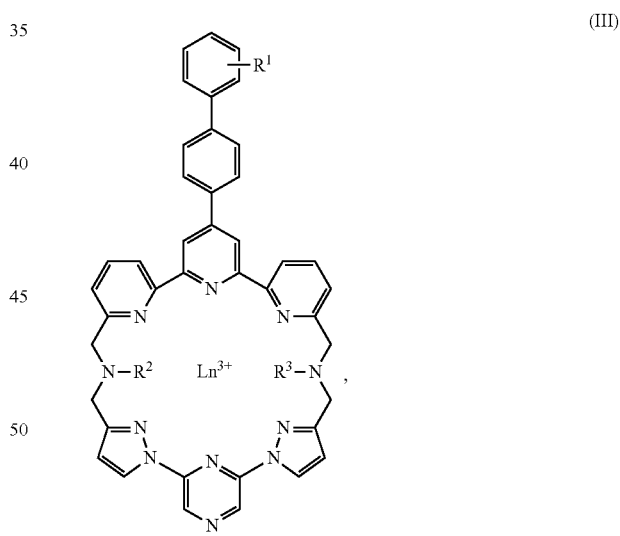

(III)

wherein:

R¹ is a nitro group or an optionally substituted amino group;

R² and R³ each independently is a carboxyalkyl group; and

Ln represents a rare-earth metal.

(8) The rare-earth fluorescent complex according to (6) or (7), wherein the substituent of amino group in R¹ of the general formula (I) is a group bind to the substance to be labeled.

(9) The rare-earth fluorescent complex according to any one of (4)-(8), wherein the rare-earth metal comprised therein is either terbium or europium.

(10) A terbium complex having a ligand for the formation of the rare-earth fluorescent complex which is capable of forming a fluorescent complex with terbium, the complex can emit fluorescent light and can be excited at a wavelength of 340 nm or longer.

(11) The terbium complex according to (10), of which ligand is a compound represented by the following general formula (IV):

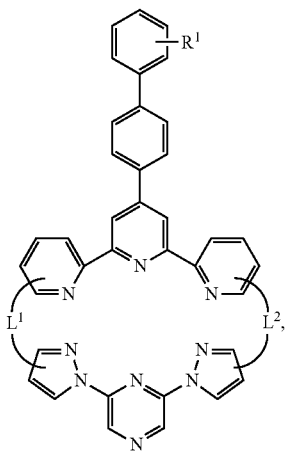

(IV)

wherein:
$R^1$ is a nitro group or an optionally substituted amino group;
$L^1$ and $L^2$ independently is a straight or branched chain $C_1$-$C_6$ alkylene group having at least one carbon atom optionally substituted with a nitrogen atom, each of which links both rings and optionally comprises an anionic group to neutralize positive charges of rare-earth ions; and
Ln represents a rare-earth metal.

(12) The terbium complex according to (10) or (11), of which ligand is a compound represented by the following general formula (I):

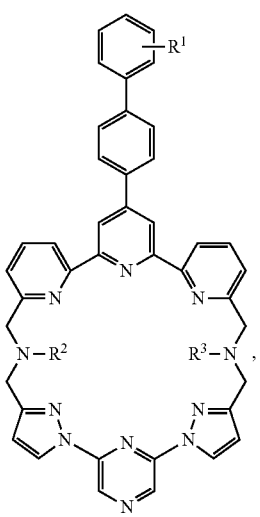

(I)

wherein:
$R^1$ is a nitro group or an optionally substituted amino group;
$R^2$ and $R^3$ each independently is a carboxyalkyl group.

(13) A fluorescent labeling agent to label a substance to be labeled, comprising a rare-earth fluorescent complex according to any one of (4)-(12).

(14) The fluorescent labeling agent according to (13), wherein a substance to be labeled is a biomaterial or a physiologically active substance.

(15) The fluorescent labeling agent according to (14), wherein the biomaterial or the physiologically active substance is an enzyme, a protein, a hormone, a peptide, a nucleic acid, a nucleic acid probe, an oligonucleotide or a drug (including antibiotics).

(16) A fluorescent labeling method to label a substance to be labeled, wherein the rare-earth fluorescent complex according to any one of (4)-(12) is bonded to a substance to be labeled via a binding group.

(17) The biomaterial or the physiologically active substance labeled with the fluorescent labeling agent according to (13).

(18) The labeled biomaterial or the physiologically active substance according to (17), wherein the biomaterial or the physiologically active substance is an enzyme, a protein, a hormone, a peptide, a nucleic acid, a nucleic acid probe, an oligonucleotide or a drug (including antibiotics).

(19) A fluorescent assay comprising binding the fluorescent labeling agent according to (13) to a substance to be labeled via the binding group, thereby labeling the substance to be labeled, and measuring fluorescence of the fluorescent labeling agent.

(20) The fluorescent assay according to (19), wherein the fluorescent assay is a time-resolved fluorescence assay.

(21) The fluorescent assay according to (20), wherein the time-resolved fluorescence assay is a time-resolved fluorescent immunoassay, a time-resolved fluorescent DNA hybridization assay, a time-resolved fluorescent microscopic imaging, or time-resolved fluorescent chromatography.

(22) A kit for fluorescent assay comprising the fluorescent labeling agent according to (13).

The present invention relates to a rare-earth fluorescent complex having a ligand for the formation of a rare-earth fluorescent complex which can form a complex with 2 or more of rare-earth metals; can emit fluorescence and can effectively be excited at a wavelength of 340 nm or longer. In more detail, the present invention relates to the rare-earth fluorescent complex having a cyclic ligand comprising a 4-biphenyl-2,2':6',2"-terpyridine skeleton and a 2,6-bis-(3'-aminomethyl-1'-pyrazolyl)-pyrazine skeleton.

The ligand of the rare-earth fluorescent complex of the present invention is characterized to form a cyclic compound wherein the left and right pyridine rings in 4-biphenyl-2,2': 6',2"-terpyridine skeleton of the following general formula (V):

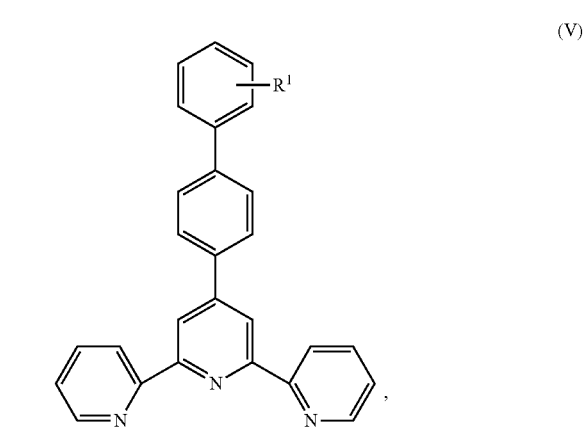

(V)

wherein:

R$^1$ is a hydrogen atom or a substituent (group) on the biphenyl ring;

are bonded to 2,6-bis(3'-aminomethyl-1'-pyrazolyl)pyrazine skeleton of the following general formula (VI):

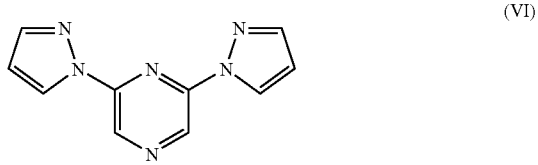

(VI)

via an appropriate binding group.

The binding group which binds the left and right pyridine rings of terpyridine skeleton of the general formula (III) and the pyrazine skeleton of the general formula (IV) may be any group that can chemically bind both structures in keeping an appropriate distance for rare-earth metal to be coordinated, and can maintain stability of a chemical substance.

A preferable cyclic compound is a large cyclic compound represented by the following general formula (IV):

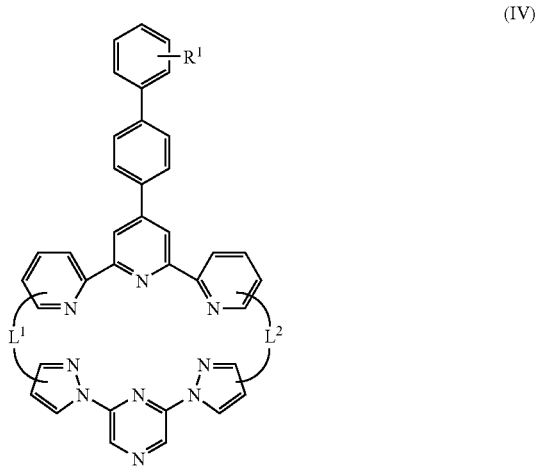

(IV)

wherein:

R$^1$ is a nitro group or an optionally substituted amino group;

L$^1$ and L$^2$ each independently is a straight or branched chain C$_1$-C$_6$ alkylene group having at least one carbon atom optionally substituted with a nitrogen atom, each of which links both rings and optionally comprises an anionic group to neutralize positive charges of rare-earth ions.

The straight or branched chain C$_1$-C$_6$ alkylene group with at least one carbon atom optionally substituted with a nitrogen atom in L$^1$ and L$^2$, includes a straight or branched chain C$_1$-C$_6$ alkylene group such as a methylene group, an ethylene group, a propylene group and a butylene group, preferably includes a straight or branched chain C$_2$-C$_4$ alkylene group, or the alkylene group wherein at least one carbon atom is substituted with a nitrogen atom. The nitrogen substituted alkylene group is represented by the following general formula:

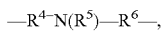

R$^4$ and R$^6$ each independently is a straight or branched chain C$_1$-C$_5$ alkylene group, and R$^5$ is a straight or branched chain C$_1$-C$_5$ alkylene group optionally having an anionic group to neutralize positive charges of rare-earth ions.

The straight or branched chain C$_1$-C$_5$ alkylene group of the said general formula, includes a straight or branched chain C$_1$-C$_5$ alkylene group such as a methylene group, an ethylene group, a propylene group, preferably a straight or branched chain C$_1$-C$_3$ alkylene group, more preferably a methylene group or an ethylene group.

In one embodiment, R$^1$ in the general formula (V) or (IV) may be a hydrogen atom, but preferably is a group that can be converted to a functional group capable of binding the rare-earth fluorescent complex of the present invention (as a fluorescent labeling agent) to a substance to be labeled. The preferable functional group includes, but not limited to, a nitro group or an amino group which contains a nitrogen atom.

In another embodiment, the anionic group to neutralize positive charges of rare-earth ions in L$^1$ and L$^2$ of the large cyclic compound represented by the general formula (IV) supra, preferably is further substituted with a group having an anionic functional group to neutralize the positive charges of the ionized rare-earth metal. The functional group which becomes an anionic group can be an acidic group such as a carboxyl group and a sulfonic acid group, or a neutral group such as a hydroxyl group, but preferably is a carboxyl group which can easily be produced and give a compound with good stability. The preferable group having a functional group which becomes an anionic group includes, but not limited to, a carboxyalkyl group.

The preferable ligand in the rare-earth fluorescent complex of the present invention includes the compound of the general formula (IV) or (I), or the salt thereof.

R$^1$ in the general formula (I) or (IV) is a substituent (group) on biphenyl ring with which either one of the biphenyl ring can be substituted. R$^1$ can be a substituent with which a certain position of the biphenyl ring is substituted, or R$^1$ can be a mixture of substituents with which various positions of biphenyl ring are substituted. R$^1$ may be one or, if necessary, 2 or more substituent group(s). R$^1$ may be the same or different if presented in two or more substituent groups.

The optionally substituted amino group represented by R$^1$ in the general formula (I) or (IV) includes an unsubstituted amino group or an amino group substituted with a group capable of binding to a substance to be labeled (the labeled substance). The group which is capable of binding to a substance to be labeled (the labeled substance) includes, but not limited to, any group that can react with a reactive functional group of the labeled substance to form a covalent bond and can stably bind to the amino group. The substituted amino group represented by R$^1$ of the general formula (I) preferably includes, for example, an isothiocyanate group, a halogeno acetyl amino group, a hydrazino group, a (4,6-dihalogeno-1,3,5-triazene-2-yl)-amino group, a carboxyl group and the like. The halogen group in the halogeno acetyl amino group and the (4,6-dihalogeno-1,3,5-triazine-2-yl)amino group includes —Cl, —Br, —I and the like.

The carboxyalkyl group represented by R$^2$ or R$^3$ of the general formula (I) includes a straight or branched chain C$_1$-C$_5$ alkyl group, preferably C$_1$-C$_3$ alkyl group substituted with a carboxyl group, for example, a carboxymethyl group, a 1-carboxyethyl group, a 2-carboxyethyl group and the like. The carboxyalkyl groups preferably include a carboxymethyl group.

The examples of the salts according to the compound of the present invention represented by the general formula (I) include alkali metal salts such as sodium and potassium salts with respect to the acidic groups such as carboxyl groups; as well as acid salts such as hydrochloric acid and sulfuric acid salts with respect to the basic groups such as amino groups.

The compound of the present invention represented by the general formula (I) or (IV) is capable of binding to a rare-earth metal ion to form a stable rare-earth metal complex of the general formula (II) or (III).

$R^1$, $L^1$ and $L^2$ in the general formula (II) and $R^1$, $R^2$ and $R^3$ in the general formula (III) indicate the same as those of the general formula (I) or (IV). The rare-earth ion may be selected depending on the fluorescent intensity, fluorescent wavelength or fluorescent lifetime of the complex to be formed; preferably are the trivalent lanthanoid ions; more preferably are the trivalent europium ion, trivalent terbium ions, trivalent samarium ions, trivalent dysprosium ions, or the like.

The rare-earth metal complex of the present invention is characterized by having a ligand for the formation of a rare-earth fluorescent complex which forms a complex with 2 or more of rare-earth metals; emits fluorescence and can effectively be excited at a wavelength of 340 nm or longer; wherein a terbium complex can be any which has a ligand capable of forming complex with terbium that can emit fluorescent light and can be excited at a wavelength of 340 nm or longer. The ligand of the terbium complex includes compounds represented by the general formula (I) or (IV).

A complex formed from rare-earth metal ion and a compound of the present invention represented by the general formula (I) or (IV) is a fluorescent complex. Accordingly, the resulting rare-earth fluorescent complex of the present invention can be used as a fluorescent labeling agent.

A fluorescent labeling agent of the present invention comprising a rare-earth metal complex of the present invention, can comprise any the following selected from the compound isolated as a rare-earth metal complex; a solution comprising said rare-earth metal complex; or a solution comprising a rare-earth metal ion and the compound of the present invention represented by the general formula (I) or (IV).

The fluorescent labeling method of the present invention is characterized by using the fluorescent labeling agent of the present invention. The method can be performed by labeling various substances with the fluorescent labeling agent of the present invention. The fluorescent labeling can be carried out by either one of the following procedures: (1) reacting a substance to be labeled with the compound of the present invention represented by the general formula (I) or (IV), followed by forming a complex by reacting with appropriate rare-earth metal ions and (2) reacting all of "a substance to be labeled", "a compound of the present invention represented by the general formula (I) or (IV)" and "a rare-earth metal ion" together at once, thereby performing the formation of a complex and fluorescent labeling in parallel.

A method for binding a substance to be labeled with any one of the compound of the present invention represented by the general formula (I)-(IV) can be carried out by reacting an optionally substituted amino group of $R^1$ in the general formula (I)-(IV) with a functional group such as amino group or hydroxyl group of substance to be labeled by a known method. A substance can be labeled with the fluorescent labeling agent of the present invention by either procedure: a) through crosslinking of an amino group of the present invention or an amino group of the ligand using a bivalent reagent (bridging agent), or b) by further modifying the amino group into the derivative thereof. The bridging agents, for example, include the following compounds:

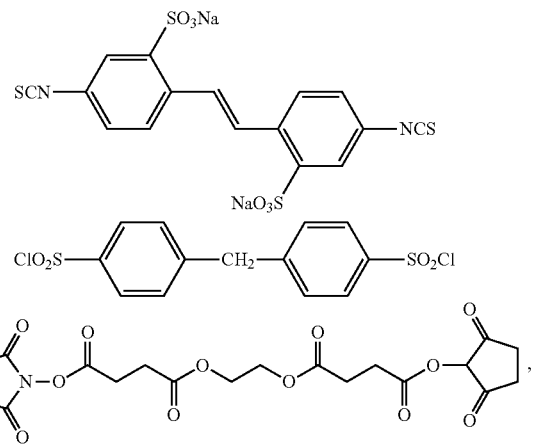

which are useful when targeting an amino group, and the followings are useful when targeting a thiol group:

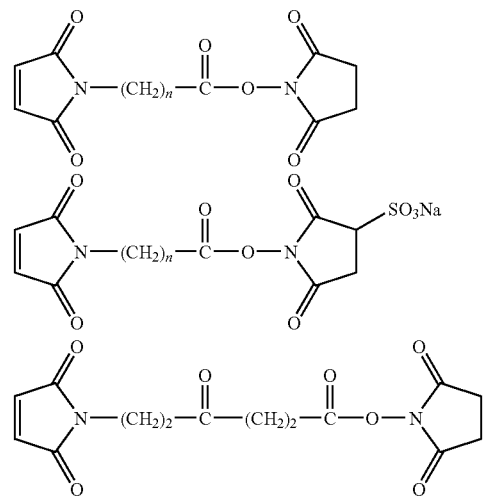

The substance to be labeled used for the present invention is not particularly limited, but a biomaterial, a physiologically active substance, and other chemical substances, etc. may be used extensively. It is not limited in molecular size or existing phase (solution or solid) thereof, nor limited either to a single compound or a composition of matter. A substance to be labeled with the labeling agent of the present invention can be any but has at least one reactive group that can covalently bind to a fluorescent labeling agent of the present invention, or has a group whereto said reactive group can be introduced.

The biomaterial or physiologically active substance which can be labeled with a fluorescent labeling agent of the present invention include, for example, an enzyme, a protein, a peptide (oligopeptide or polypeptide), sucrose, glycoprotein, a hormone, a lipid, a nucleic acid, a nucleic acid derivative, a nucleic acid probe, an oligonucleotide, a cell, a lipid compound, an amino acid, a drug (including antibiotics), or the like.

The specific examples of the proteins are an antibody and a derivative thereof, an antigen and a derivative thereof, an avidin (including strepto avidin), serum albumin, various haptens, hormones, protein A, protein G or the like. Other chemical substances include, for example, agricultural chemicals, daily use chemicals, chemical regents, industrial chemicals, or the like.

The fluorescent assay of the present invention is characterized in that the measurement is performed by using a rare-earth metal complex comprising a compound the of present invention represented by the general formula (I) and rare-earth metal ions as a fluorescent labeling agent; or by fluorescent labeling various substances with a compound of present invention represented by the general formula (I) and rare-earth metal ions. The representative fluorescent assay includes, for example, a time-resolved fluorescence assay. The time-resolved fluorescence assay includes several applications such as a time-resolved fluorescence immunoassay, a DNA hybridization assay, a chromatography, a fluorescent microscopy.

In the invention, a fluorescent assay reagent is the reagent used for the fluorescent assay of the present invention as described above characterized by comprising a rare-earth metal complex which comprises a compound of the present invention represented by the general formula (I) and rare-earth metal ions as a fluorescent labeling agent; or comprising a compound of the present invention represented by the general formula (I) and rare-earth metal ions.

The fluorescent assay reagents of the present invention can be used for the assays of biomaterials, physiologically active substances or other chemical substances, but more effectively used for the assays of biomaterials and physiologically active substances. The examples of biomaterials and physiologically active substances are specifically described as above.

The kit of reagents according to the present invention can be used for the above described fluorescent assays, comprising a rare-earth metal complex which comprises a compound of the present invention represented by the general formula (I) and rare-earth metal ions as a fluorescent labeling agent, or comprising a compound of the present invention represented by general formula (I) and rare-earth metal ions.

The method for production of a compound represented by the general formula (I), and the starting material thereof are not particularly limited, but any of the compounds can be produced by suitably combining the ordinary organic synthesis methods. The structural identification of a product can be carried out by the ordinary chemical structure analysis of organic compounds, such as $^1$H NMR and organic elemental analysis.

The process for the production of a compound of the present invention represented by the general formula (I) can be illustrated by the following reaction scheme, wherein $R^1$ is an amino group, $R^2$ and $R^3$ are both carboxymethyl groups:

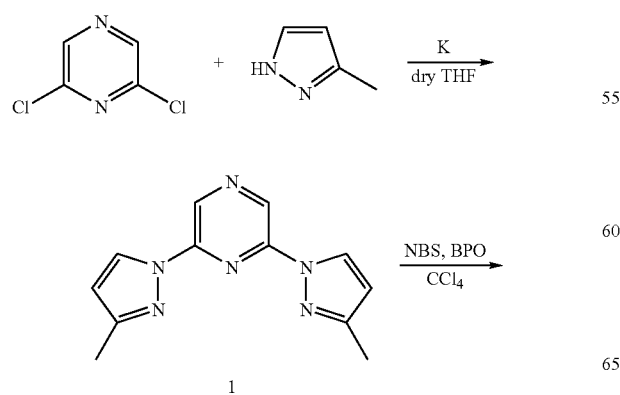

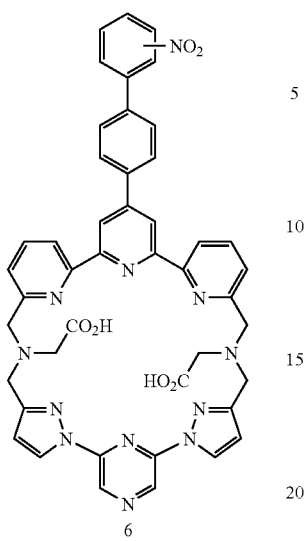

6

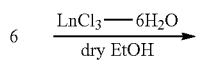

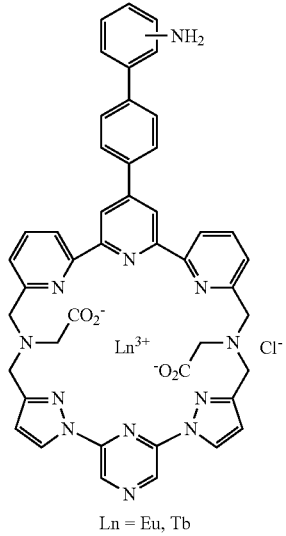

Ln = Eu, Tb
Amino-BTPDA-Ln³⁺
(8)

The compound 1 is produced by reacting 3-methylpyrazole with 2,6-dichloro pyradine, followed by halogenating the methyl group to obtain the halogeno-methyl compound 2. The N-alkoxycarbonylalkyl compound 3, i.e. the compound having the pyrazine skeleton represented by the general formula (IV), is produced by converting the halogeno-methyl into an alkoxycarbonyl alkyl group by using ethyl amino acetate. Then, this N-alkoxycarbonyl alkyl compound 3 is reacted with a halogeno-methyl compound 4 having the terpyridine structure represented by the general formula (III) to produce the cyclic ligand compound 5 of the present invention. The halogeno-methyl compound 4 having the terpyridone structure represented by the general formula (III) used in this reaction can be produced by the method, for example, described in Patent Reference 5 (WO 2003/076938). of the present invention represented by the general formula (I) by hydrolysis of the ester group of compound 5. The compound 5 or 6 can further be converted into the corresponding amino compound by reducing the nitro group with such as catalytic reduction. The corresponding substituted amino compounds can be obtained by substituting the amino group of the amino compound with an appropriate substituent.

The compound of the present invention represented by the general formula (I) can be produced by this manner or by the manner similar to this. The compound can be obtained in the form of salt, if necessary.

The rare-earth metal complex 7 of the present invention represented by the general formula (II) can be produced by dissolving the compound of the present invention represented by the general formula (I) produced as above in a solvent such as ethanol, whereto admixing a compound containing rare-earth metal ions such as rare-earth metal chloride. Further, the corresponding amino compound 8 can be obtained, if necessary, by reducing the nitro group of the rare-earth metal complex 7 by such as catalytic reduction. The corresponding substituted amino compounds can be obtained by substituting the amino group of the amino compound with an appropriate substituent.

EFFECTS OF THE INVENTION

The present invention is to provide a novel compound having a binding group which binds to a substance to be

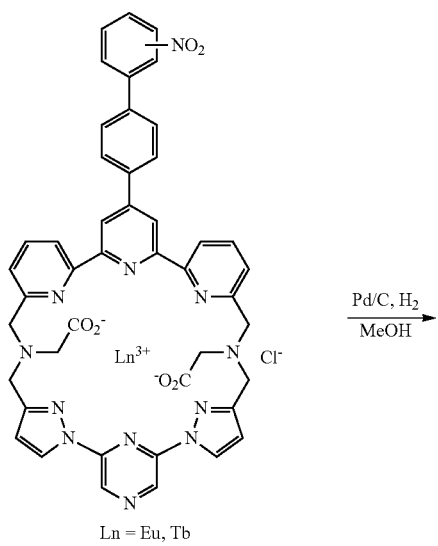

Ln = Eu, Tb
Nitro-BTPDA-Ln³⁺
(7)

labeled (e.g., a biomaterial, a physiologically active substance, etc.) and easily forming a complex with rare-earth metal ions; and a rare-earth metal complex comprising thereof. The resulting rare-earth metal complex is stable in an aqueous solution, and has a sufficient fluorescent intensity and a long fluorescent lifetime, can form a complex with 2 or more rare-earth metals, moreover, can emit fluorescent light at a wavelength of 340 nm or longer commonly provided by an ordinary laser light source. Accordingly, the rare-earth metal complex of the present invention enables the direct labeling of an enzyme, a protein, a peptide (oligopeptide or polypeptide), a hormone, a nucleic acid probe, oligonucleotide, or a drug (including antibiotics), other organic chemical compounds, or the like which has a functional group such as an amino group and a mercapto group in an aqueous solution. The fluorescent labeling agent of the present invention is particularly useful for the fluorescent assay which requires 2 or more fluorescent labeling agents respectively having different fluorescent wavelengths.

In another embodiment, the compound of the present invention represented by the general formula (I) can form an extremely stable labeling complex through a covalent bond with a substance to be labeled (including particularly an enzyme, a protein, a peptide (oligopeptide or polypeptide), a hormone, a nucleic acid probe, oligonucleotide, a drug (including antibiotics) and other organic chemical compounds, etc. having an amino group and a mercapto group, etc.). The resulting labeling complex was further reacted with rare-earth metal ions to obtain an extremely stable rare-earth fluorescent labeling complex which also has an extremely long fluorescent lifetime and a strong fluorescent intensity, and is directly applicable to such as a time-resolved fluorescence immunoassay and a DNA hybridization assay.

Figure 1:
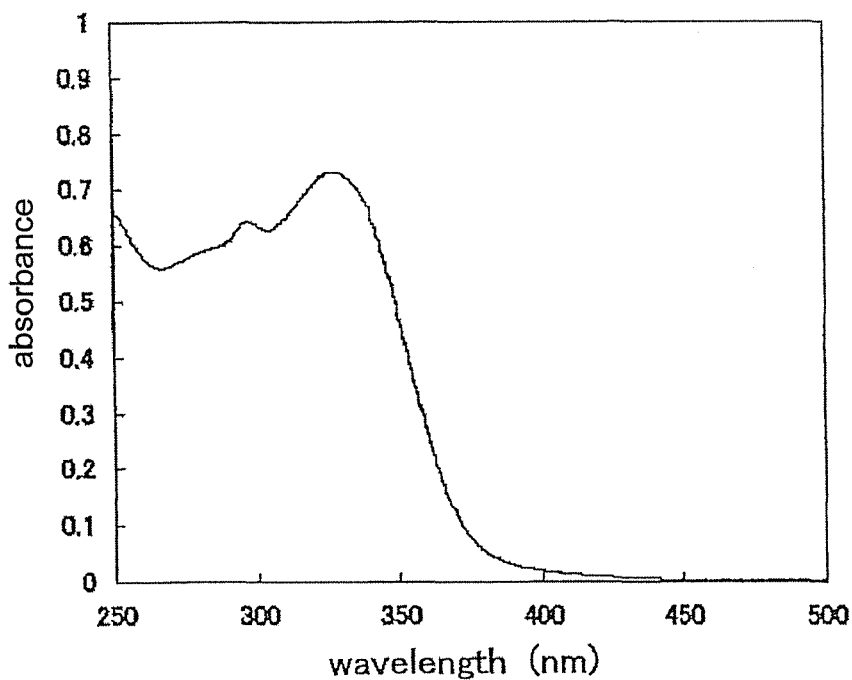
FIG. 1 is a chart showing absorption spectrum of nitro-BTPDA-Eu compound, which is one of rare-earth metal complexes of the present invention. The abscissa of FIG. 1 indicates a wavelength (nm) while the ordinate indicates the absorbance. The solvent is methanol and the concentration of the complex is $1.5 \times 10^{-5}$ M.

The present invention is illustrated in more detail by the following examples, but should not be construed to be limited thereto.

REFERENTIAL EXAMPLE 1

Preparation of ({4'-(nitro-biphenyl-4"-yl)-2,2:6',2"-terpyridine-6,6"-di-yl}bis(bromo methyl)), the compound indicated as compound 4 in the above described production chart.

The title compound was produced in the same manner as described in Patent Reference 5 (WO 2003/076938) as follows:

(1) Preparation of 4'-(biphenyl-4"-yl)-2,2':6',2"-terpyridine

N-[2-(pyrid-2'-yl)-2-oxoethyl]-pyridinium iodide (16.3 g, 50 mmol), (E)-3-(biphenyl-4"-yl)-1-(pyrid-2'-yl)-2-propenone (14.26 g, 50 mmol) and ammonium acetate (23.1 g) were added to 500 mL of dry methanol, and the solution was refluxed for 24 hrs with stirring. The reaction solution was cooled down. The resulting precipitate was filtered out, thoroughly washed with cold methanol, recrystallized from the acetonitrile solution, and the desired compound was obtained. The yield after drying in vacuo was 49.3%.

Result of the elemental analysis ($C_{27}H_{19}N_3$)
Calculated value (%), C=84.13, H=4.97, N=10.90
Found value (%), C=84.01, H=4.82, N=10.88)
The results of the $^1$H-NMR spectrometry confirmed the synthesis of the desired compound.
$^1$H-NMR (CDCl$_3$): δ 8.80 (s, 2H), 8.75 (d, J=4.6 Hz, 2H), 8.69 (d, J=7.8 Hz, 2H), 8.01 (d, J=8.6 Hz, 2H), 7.89 (t, J=7.6 Hz, 2H), 7.75 (d, J=8.2 Hz, 2H), 7.68 (d, J=6.9 Hz, 2H), 7.48 (t, J=6.9 Hz, 2H), 7.41-7.33 (m, 3H).

(2) Preparation of 4'-(biphenyl-4'"-yl)-2,2':6',2"-terpyridine-1,1"-dioxide

The compound obtained in step (1) (19.27 g, 50 mmol) was dissolved in 700 mL of CH$_2$Cl$_2$. To this solution was added 50 g of 3-chloro peroxybenzoic acid, followed by stirring at room temperature for 20 hrs. The reaction solution was washed 3 times with 300 mL of 10% aqueous solution of Na$_2$CO$_3$ and dried the organic phase with Na$_2$SO$_4$, and the solvent was evaporated under reduced pressure. The resulting product was dissolved in 300 mL of methanol, and filtered off the contamination, and the solvent was removed by evaporation under reduced pressure. The product was washed well with acetonitrile, dried in vacuo to obtain the title product. The yield was 91.4%. The results of the $^1$H-NMR spectrometry confirmed the synthesis of the desired compound.
$^1$H-NMR (CDCl$_3$): δ 9.29 (s, 2H), 8.38 (d, J=6.6 Hz, 2H), 8.25 (d, J=8.2 Hz, 2H), 7.94 (d, J=8.6 Hz, 2H), 7.72 (t, J=8.6 Hz, 2H), 7.66 (d, J=6.9 Hz, 2H), 7.50-7.43 (m, 2H), 7.41-7.29 (m, 5H).

(3) Preparation of 4'-(biphenyl-4'"-yl)-2,2':6',2"-terpyridine-6,6"-dicarbonitrile The compound obtained in step (2) (15.65 g, 37.5 mmol) and (CH$_3$)$_3$SiCN (37.2 g, 375 mmol) were added to 450 mL of CH$_2$Cl$_2$, followed by stirring at room temperature for 20 min. And 150 mmol of benzoyl chloride was added dropwise over a period of about 20 min. The reaction solution was stirred at room temperature for 24 hrs, and then the solvent was evaporated under reduced pressure until it became a half in volume. To the remaining solution was added 600 mL of 10% aqueous solution of K$_2$CO$_3$ and stirred at room temperature for 1 hr. The resulting precipitate was filtered out, washed with water and then cold CH$_2$Cl$_2$, dried in vacuo to obtain the desired product. The yield was 80.8%. The results of the $^1$H-NMR spectrometry confirmed the synthesis of the desired compound.
$^1$H-NMR (DMSO-d$_6$): δ 8.99 (d, J=7.6 Hz, 2H), 8.75 (s, 2H), 8.31 (t, J=7.9 Hz, 2H), 8.20 (d, J=7.6 Hz, 2H), 8.10 (d, J=7.6 Hz, 2H), 7.92 (d, J=8.2 Hz, 2H), 7.78 (d, J=7.6 Hz, 2H), 7.54-7.42 (m, 3H).

(4) Preparation of dimethyl 4'-(biphenyl-4'"-yl)-2,2':6',2"-terpyridine-6,6"-dicarboxylate To the mixture of H$_2$SO$_4$ 90 mL/CH$_3$COOH 90 mL/H$_2$O 20 mL was added 8.71 g (20 mmol) of the nitrile compound obtained in step (3), and the solution was stirred at 90-100° C. for 24 hrs. The reaction solution was added to 800 g of ice, and stirred. The resulting precipitate was filtered out, washed fully with water and ethanol, dried in vacuo to obtain 9.13 g of a hydrolyzed product.

To 600 mL of dried methanol cooled with ice-water was added 24 g of thionyl chloride SOCl$_2$ and stirred for 15 min. And to the solution was added 9.13 g of the hydrolyzed product previously obtained, and refluxed for 24 hrs with stirring. The solvent was evaporated under reduced pressure, the resulting product was dissolved in 1000 mL of chloroform CHCl$_3$, and the organic layer was washed fully with 15% aqueous solution of NaHCO$_3$, and dried over Na$_2$SO$_4$. The solvent was evaporated under reduced pressure, and the product was purified with a silica gel column (eluent: CH$_2$Cl$_2$—CH$_3$OH=99:1 w/w). The desired compound was obtained by crystallization from the toluene solution. The yield was 48.5%.

Result of elemental analysis ($C_{31}H_{23}N_3O_4$):
Calculated value (%), C=74.24, H=4.62, N=8.38
Found value (%), C=74.15, H=4.55, N=8.38
The results of the $^1$H-NMR spectrometry further confirmed the synthesis of the desired compound.
$^1$H-NMR (CDCl$_3$): δ 8.88 (s, 2H), 8.86 (d, J=7.9 Hz, 2H), 8.20 (d, J=7.6 Hz, 2H), 8.06 (d, J=7.9 Hz, 2H), 8.00 (d, J=7.2 Hz, 2H), 7.78 (d, J=6.6 Hz, 2H), 7.70 (d, J=6.9 Hz, 2H), 7.52-7.30 (m, 3H), 4.07 (s, 6H).

(5) Preparation of 4'-(biphenyl-4'"-yl)-2,2':6',2"-terpyridine-6,6"-dihydroxy methyl To 400 mL of dry ethanol were added the methoxycarbonyl compound obtained in step (4) (7.02 g, 14 mmol) and 3.02 g of NaBH$_4$, and the solution was stirred at room temperature for 3 hrs, and refluxed for 1 hr. The solvent was evaporated under reduced pressure, and the resulting product was added to 200 mL of saturated aqueous solution of NaHCO$_3$ and the solution was heated until boiling with stirring. After cooling down, the precipitate was filtered out, washed fully with water, dried in vacuo to obtain the desired product. The yield was 92.0%. The results of the $^1$H-NMR spectrometry confirmed the synthesis of the desired compound.
$^1$H-NMR (DMSO-d$_6$): δ 8.75 (s, 2H), 8.55 (d, J=7.9 Hz, 2H), 8.07-8.00 (m, 4H), 7.92 (d, J=8.2 Hz, 2H), 7.78 (d, J=7.2 Hz, 2H), 7.61 (d, J=7.9 Hz, 2H), 7.57-7.50 (m, 2H), 7.46-7.40 (m, 1H), 5.57 (t, J=5.9 Hz, 2H), 4.74 (d, J=4.6 Hz, 4H).

(6) Synthesis of 4'-(4'"'-nitro-biphenyl-4'"-yl)-2,2':6',2"-terpyridine-6,6"-dihydroxymethyl The compound obtained in step (5) (1.78 g, 4 mmol) was added to 30 mL of acetic anhydride, followed by stirring at 60° C. for 15 hrs. The solvent was evaporated under reduced pressure, and 20 mL of acetic anhydride was added to the residue. To the solution was added dropwise a mixture of 20 mL of acetic acid and 3 mL of fuming nitric acid while cooling in an external ice/water bath. The solution was stirred for 2 hrs in an external ice/water bath, and further stirred at room temperature for 24 hrs. The reaction solution was added to 250 mL of water, and stirred for 1 hr, the solution was extracted 3 times with 100 mL of CHCl$_3$. The CHCl$_3$ solution was washed with 5% aqueous solution of NaHCO$_3$ and dried over Na$_2$SO$_4$, and the solvent was evaporated under reduced pressure. The resulting residue was added 150 mL of ethanol, 10 g of KOH and 15 mL of water, and the mixture was stirred at room temperature for 36 hrs. Then to the reaction mixture was added 300 mL of water, and the precipitate was collected by centrifugation. The precipitate was dried in vacuo for 5 hrs, and washed fully with water and dried in vacuo to obtain the desired nitro compound. The yield was 90.7%. $^1$H-NMR confirmed the resulting product to be a mixture of the desired compound and 4'-(2''''-nitro-biphenyl-4'''-yl)-2,2':6',2''-terpyridine-6,6''-dihydroxymethyl.

$^1$H-NMR (DMSO-$d_6$): δ 8.81-8.79 (m, 2H), 8.61 (d, J=7.9 Hz, 2H), 8.37 (d, J=7.2 Hz, 1H), 8.17-8.03 (m, 6H), 7.88-7.80 (m, 1H), 7.75-7.58 (m, 4H), 4.78 (s, 4H).

(7) Preparation of 4'-(4''''-nitro-biphenyl-4'''-yl)-2,2': 6',2''-terpyridine-6,6''-dibromo methyl The compound (1.78 g, 3.63 mmol) obtained in (6) was dissolved in a solvent mixture of 200 mL of THF and 80 mL of DMF, followed by the addition of 3.52 g of PBr$_3$ and the solution was refluxed for 6 hrs with stirring. The solvent was distilled out under reduced pressure, and 300 mL of CHCl$_3$ was added to the product. The organic phase was washed with 4×200 mL of a saturated aqueous solution of Na$_2$SO$_4$, and further washed with 200 mL of a 10% aqueous solution of NaHCO$_3$. The organic phase was dried over Na$_2$SO$_4$ and the solvent was evaporated under reduced pressure, and the product was purified with a silica gel column (eluent: CH$_2$Cl$_2$—CH$_3$OH=99.5:0.5 v/v). The solvent was evaporated under reduced pressure and dried in vacuo to obtain the desired bromo methyl compound. The yield was 56.3%.

Result of elemental analysis (C$_{29}$H$_{20}$Br$_2$N$_4$O$_2$):
Calculated value (%), C=56.52, H=3.27, N=9.09
Found value (%), C=56.64, H=3.32, N=9.10
Result of mass analysis (FAB-MS):
m/e, 617.3 (M++), 571.3 (M-NO$_2$)

Furthermore, $^1$H-NMR confirmed the resulting product to be a mixture of a desired compound and 4'-(2''''-nitro-biphenyl-4'''-yl)-2,2':6',2''-terpyridine-6,6''-dibromo methyl.

$^1$H-NMR (CDCl$_3$): δ 8.70 (s, 1H), 8.69 (s, 1H), 8.57 (d, J=7.9 Hz, 2H), 8.33 (d, J=8.8 Hz, 1H), 8.10-8.00 (m, 6H), 7.95 (d, J=8.2 Hz, 1H), 7.70-7.55 (m, 4H), 4.84 (s, 4H).

EXAMPLE 1

(1) Preparation of 2,6-bis-(3-methyl-pyrazol-1-yl)-pyradine [Compound 1 (Hereinafter the Compound Numbers are the Same as Those of the Production Chart)]

3-Methyl pyrazole (9.85 g, 120 mmol) was dissolved in 150 mL of dry THF, followed by the addition of potassium (4.7 g, 120 mmol) and the mixture was treated at 60° C. until no potassium could be detected, then the reaction mixture was allowed to cool to room temperature. To the solution was added 2,6-dichloro pyridine (4.46 g, 30 mmol), refluxed for 4 days, allowed to cool down, and water (75 mL) was added to the solution. THF solvent was distilled out under reduced pressure, and the precipitate was separated by suction filtration. The precipitates were washed with water to obtain the desired product. The yield was 85.5%. $^1$H-NMR confirmed the production of the desired compound.

$^1$H-NMR (CDCl$_3$, 400 MHz): δ 2.41 (s, 6H), 6.33 (d, J=2.4 Hz, 2H), 8.38 (d, J=2.4 Hz, 2H), 9.08 (s, 2H).

EXAMPLE 2

(2) Preparation of 2,6-bis(3-bromo methyl-pyrazol-1-yl)-pyradine [Compound 2]

The compound 1 (2.16 g, 9 mmol) obtained in Example 1 and N-bromo succinimide (3.2 g, 18 mmol) were added to carbon tetrachloride (200 mL). Benzoyl peroxide (50 mg) was added to this mixture, and it was refluxed for 20 hrs. The reaction solution was allowed to cool to room temperature, and further cooled down with water. The solid was separated by suction filtration, and the filtrate was condensed under reduced pressure until the volume of the solvent became 10-20 mL. The remaining solution was cooled down in a freezer (1 hr), the resulting precipitate was separated by suction filtration, and washed with hexane. After drying in vacuo for 1 hr, it was recrystallized from carbon tetrachloride solution, and the desired product was obtained after washed with hexane and dried under reduced pressure. The yield was 30.1%. $^1$H-NMR confirmed the production of the desired compound.

$^1$H-NMR (CDCl$_3$, 300 MHz): δ 4.57 (s, 4H), 6.62 (d, J=2.7 Hz, 2H), 8.44 (d, J=2.7 Hz, 2H), 9.16 (s, 2H).

EXAMPLE 3

(3) Preparation of 2,6-bis-(3-[(N-ethoxycarbonylmethyl)-aminomethyl]-pyrazol-1-yl)-pyradine [Compound 3]

The compound 2 (0.76 g, 2.0 mmol) obtained in Example 2 and glycine ethyl ester hydrochloride (1.4 g, 10 mmol) were added to dry acetonitrile (150 mL). Then, potassium carbonate (2.1 g, 15 mmol) was added to the solution, and it was refluxed for 24 hrs with stirring. The resulting precipitate was separated by suction filtration, washed with a small volume of chloroform, and the solvent was evaporated from the filtrate under reduced pressure. The resulting solid was again dissolved in 200 mL of chloroform, and then washed with 10% aqueous solution of sodium chloride (200 mL×3). The organic phase was dried over sodium sulfate and the solvent was evaporated under reduced pressure. The product was purified by the thin layer chromatography method (chloroform:methanol=95:5) to obtain the desired product. The yield was 16.2%. $^1$H-NMR confirmed the production of the desired compound.

$^1$H-NMR (CDCl$_3$, 400 MHz): δ 1.29 (t, J=7.2 Hz, 6H), 2.17 (s, 2H), 3.51 (s, 4H), 3.96 (s, 4H), 4.21 (q, J=7.2 Hz, 4H), 6.51 (d, J=2.4 Hz, 2H), 8.43 (d, J=2.4 Hz, 2H), 9.14 (s, 2H).

EXAMPLE 4

(4) Preparation of nitro-BTPDA diethyl ester [Compound 5]

6,6''-Dibromo methyl-4'-(nitrobiphenyl-4-yl)-2,2':6',2''-terpyridine [compound 4] (186 mg, 0.3 mmol) obtained in Referential Example 1 and the compound 3 (133 mg, 0.3 mmol) obtained in Example 3 were added to dry acetonitrile (150 mL). To the solution was added sodium carbonate (315 mg, 3 mmol), and refluxed for 24 hrs with stirring. The precipitate was separated by suction filtration, washed with a small volume of chloroform, and then the solvent was evaporated under reduced pressure, then dissolved again in 200 mL of chloroform. The resulting solution was washed with 10% aqueous solution of sodium chloride (200 mL×3), and then the organic phase was dried over sodium sulfate and the solvent was evaporated under reduced pressure. The product was purified by the silica gel column chromatography (silica gel, chloroform-methanol=95:5 v/v) to obtain the desired product. The yield was 50.2%.

EXAMPLE 5

(5) Preparation of nitro-BTPDA compound [Compound 6]

The compound 5 (150 mg, 0.15 mmol) obtained in Example 4 and potassium hydroxide (400 mg, 6.0 mmol) were added to a small volume of ethanol and 2 mL of water, and the solution was refluxed for 24 hrs with stirring. The solvent was evaporated out from the solution, and the residue was again dissolved in small volume of water. To this solution, 3 M hydrochloric acid was added dropwise in small portions to adjust pH to 1 or less, and stirred at room temperature for 3 hrs. The precipitate was obtained by centrifugation, washed with 1% hydrochloric acid to obtain the desired product. The yield was 79.2%. ESI-MS confirmed the production of the desired compound.

ESI-Mass: m/e 841.5 $(M+H^+)^+$

EXAMPLE 6

(6) Production of nitro-BTPDA-Eu compound [Compound 7-Eu]

The compound 6 (84 mg, 0.1 mmol) obtained in Example 5 and europium chloride 6 hydrate (75.4 mg, 0.5 mmol) were added to 30 mL of methanol and the solution was refluxed for 24 hrs with stirring. The solvent was evaporated, and the residue was dissolved again in small volume of methanol, reprecipitated from diethyl ether, and left standing in a refrigerator over night. The precipitate was collected by centrifugation and dried to obtain the desired product. The yield was 50.7%. ESI-MS confirmed the production of the desired compound.

ESI-Mass: m/e 991.3 $(M-Cl^-)^+$

EXAMPLE 7

(7) Production of amino-BTPDA-Eu compound [Compound 8-Eu]

The compound 7-Eu (45 mg, 0.05 mmol) obtained in Example 6 and 10% Pd/C were added to 20 mL of dry methanol. Freeze-degas-thaw cycles were repeated to remove the dissolved oxygen from the solution. The solution was stirred at room temperature under a hydrogen atmosphere for 6 hrs, then the catalyst was filtrated off. The solution was evaporated to dryness under reduced pressure to obtain the desired product. ESI-MS confirmed the production of the desired compound.

ESI-Mass: m/e 961.3 $(M-Cl^-)^+$

EXAMPLE 8

(8) Production of nitro-BTPDA-Tb compound [Compound 7-Tb]

The compound 6 (168 mg, 0.2 mmol) obtained in Example 5 and terbium chloride 6-hydrate (150 mg, 0.5 mmol) were added to 80 mL of methanol and the solution was refluxed for 24 hrs with stirring. Then, the solvent was evaporated under reduced pressure. The residue was dissolved again in small volume of methanol, reprecipitated from diethyl ether, and left standing in a refrigerator over night. The precipitates were collected by centrifugation and dried to obtain the desired product. ESI-MS confirmed the production of the desired compound.

ESI-Mass: m/e 997.3 $(M-Cl^-)^+$

EXAMPLE 9

(9) Production of amino-BTPDA-Tb compound [Compound 8-Tb]

The compound 7-Tb (45 mg, 0.05 mmol) obtained in Example 8 and 10% Pd/C were added to 20 mL of dry methanol. Freeze-degas-thaw cycles were repeated to remove the dissolved oxygen from the solution. The solution was stirred at room temperature under hydrogen atmosphere for 6 hrs, then the catalyst was filtrated off. The solution was evaporated to dryness under reduced pressure to obtain the desired product. ESI-MS confirmed the production of the desired compound.

ESI-Mass: m/e 967.3 $(M-Cl^-)^+$

EXAMPLE 10

Figure 2:
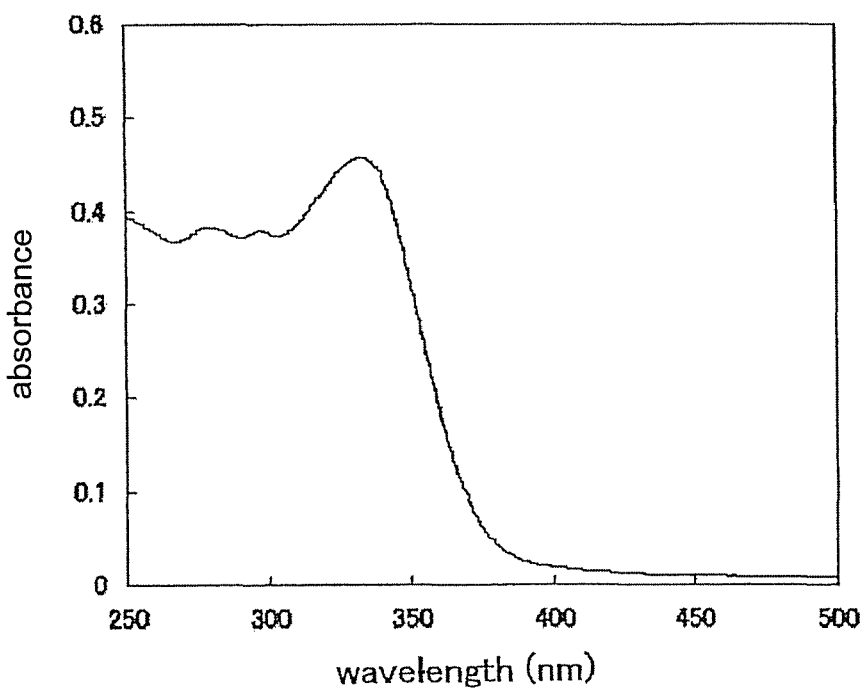
FIG. 2 is a chart showing absorption spectrum of nitro-BTPDA-Tb compound, which is one of rare-earth fluorescent complexes of the present invention. The abscissa of FIG. 2 indicates a wavelength (nm) while the ordinate indicates the absorbance. The solvent is methanol and the concentration of the complex is $1.2 \times 10^{-5}$ M.

The nitro-BTPDA-Eu compound [compound 7-Eu] obtained in Example 6 and the nitro-BTPDA-Tb compound [compound 7-Tb] obtained in Example 8 were dissolved in methanol respectively; and the absorbance with respect to each compound was measured. The absorption spectrum of the [compound 7-Eu] is shown in FIG. 1, and the absorption spectrum of the [compound 7-Tb] is shown in FIG. 2. The maximum absorption wavelengths for each rare-earth metal complexes were 328 nm and 333 nm, respectively.

EXAMPLE 11

Figure 3:
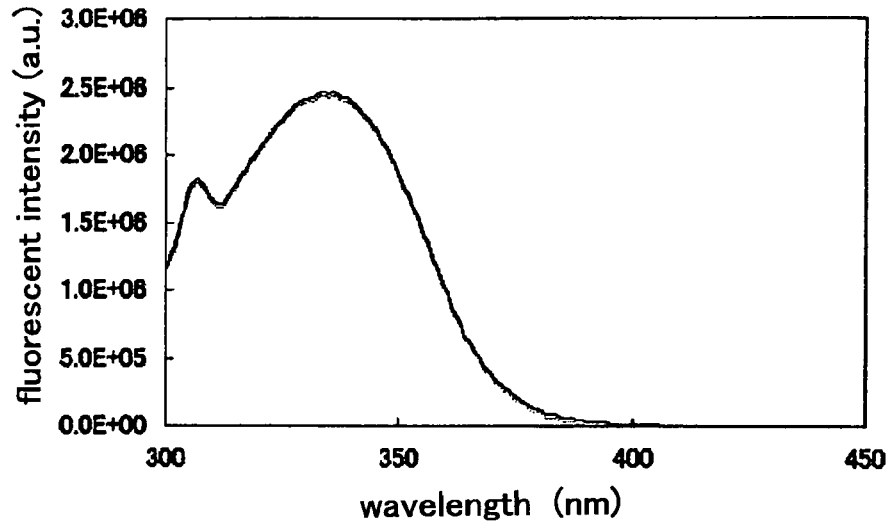
FIG. 3 is a chart showing excitation spectrum of nitro-BTPDA-Eu compound, which is one of rare-earth fluorescent complexes of the present invention. The abscissa of FIG. 3 indicates a wavelength (nm) while the ordinate indicates the fluorescence intensity. The solvent is methanol and the concentration of the complex is $1.5 \times 10^{-6}$ M, and the fluorescence at the wavelength of 613 nm was detected.
Figure 4:
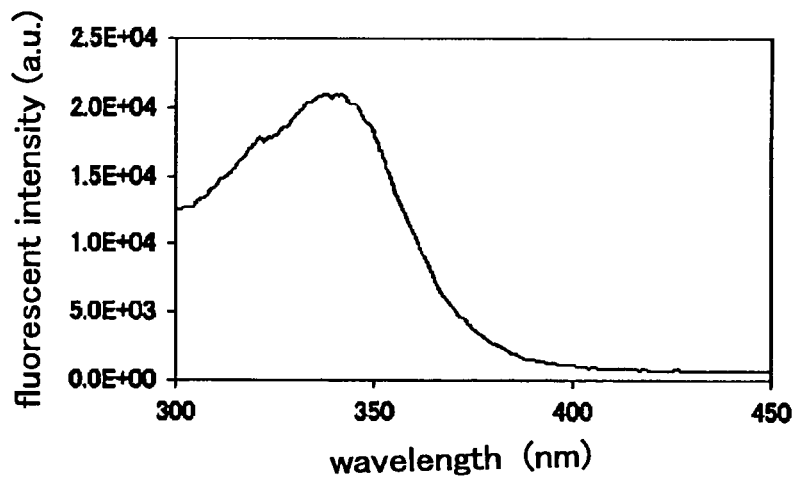
FIG. 4 is a chart showing excitation spectrum of nitro-BTPDA-Tb compound, which is one of rare-earth fluorescent complexes of the present invention. The abscissa of FIG. 4 indicates a wavelength (nm) while the ordinate indicates the fluorescence intensity. The solvent is methanol and the concentration of the complex is $1.2 \times 10^{-6}$ M, and the fluorescence at the wavelength of 545 nm was detected.
Figure 5:
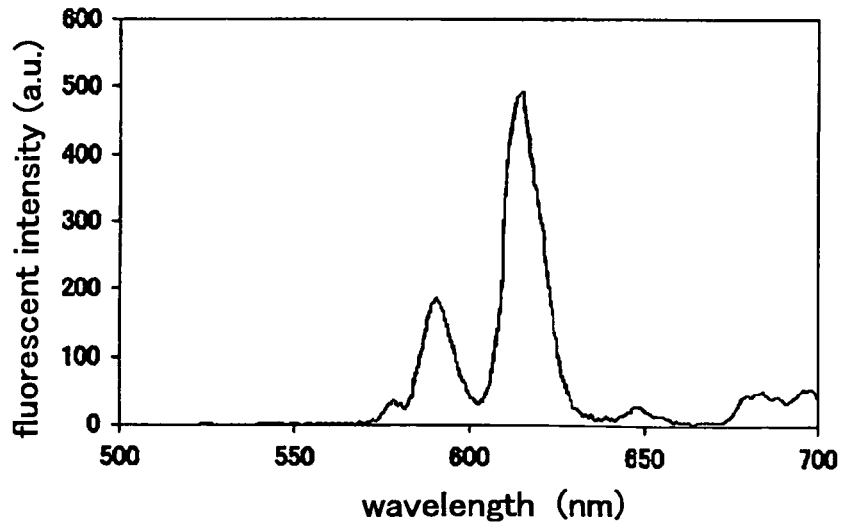
FIG. 5 is a chart showing time dissolved fluorescent spectrum of nitro-BTPDA-Eu compound, which is one of rare-earth fluorescent complexes of the present invention. The abscissa of FIG. 5 indicates a wavelength (nm) while the ordinate indicates the fluorescence intensity. The solvent is methanol and the concentration of the complex is $1.5 \times 10^{-6}$ M, and it was excited by the light at the wavelength of 330 nm. The measurements were carried out with delay time of 0.2 ms, the measurement time of 0.5 ms, with 30 times of integration.
Figure 6:
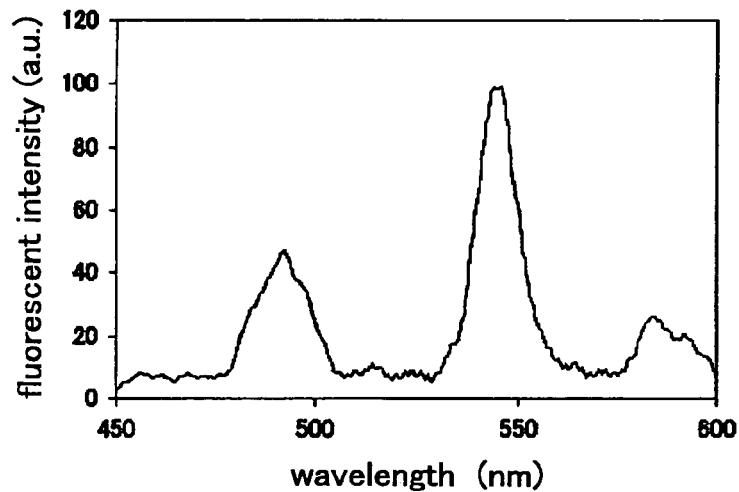
FIG. 6 is a chart showing time dissolved fluorescent spectrum of nitro-BTPDA-Tb compound, which is one of rare-earth fluorescent complexes of the present invention. The abscissa of FIG. 6 indicates a wavelength (nm) while the ordinate indicates the fluorescence intensity. The solvent is methanol and the concentration of the complex is $1.2 \times 10^{-6}$ M, and it was excited by the light at the wavelength of 330 nm. The measurements were carried out with delay time of 0.2 ms, the measurement time of 0.5 ms, with 100 times of integration.

The fluorescent characteristics in a methanol solution with respect to the nitro-BTPDA-Eu compound [compound 7-Eu] obtained in Example 6 and the nitro-BTPDA-Tb compound [compound 7-Tb] obtained in Example 8 were determined respectively. The excitation spectrum of [compound 7-Eu] is shown in FIG. 3, and the time resolved spectrum thereof is shown in FIG. 5. The excitation spectrum of [compound 7-Tb] is shown in FIG. 4 and the time resolved spectrum thereof is shown in FIG. 6. The maximum absorption wavelengths for respective rare-earth metal complexes were 336 nm and 340 nm. The fluorescence specific to each europium and terbium was detected as a result of determination of the time resolved spectrum.

EXAMPLE 12

Figure 7:
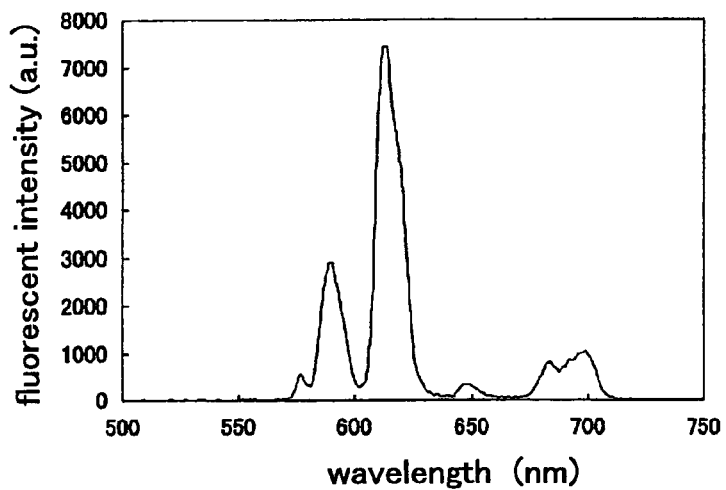
FIG. 7 is a chart showing excitation spectrum measured in a time dissolved mode of amino-BTPDA-Eu compound, which is one of rare-earth fluorescent complexes of the present invention. The abscissa of FIG. 7 indicates a wavelength (nm) while the ordinate indicates the fluorescence intensity. The solvent is methanol and the concentration of the complex is $1 \times 10^{-5}$ M, and it was excited by the light at the wavelength of 614 nm. The measurements were carried out with delay time of 0.1 ms, the measurement time of 0.5 ms, with 100 times of integration.
Figure 8:
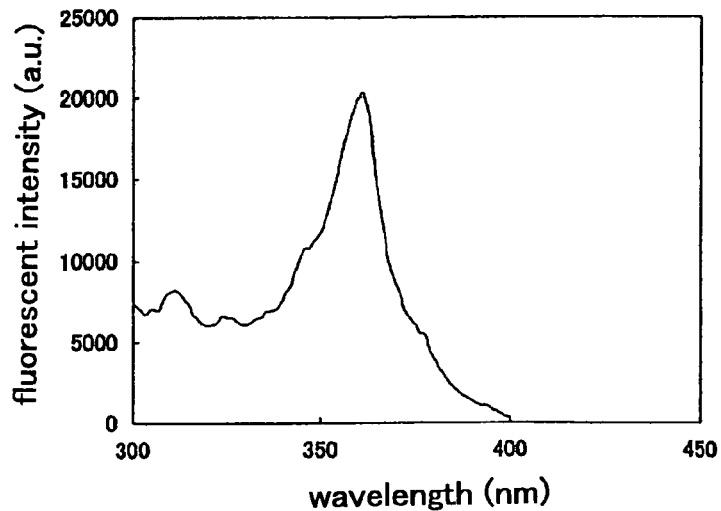
FIG. 8 is a chart showing emission spectrum measured in a time dissolved mode of amino-BTPDA-Eu compound, which is one of rare-earth fluorescent complexes of the present invention. The abscissa of FIG. 8 indicates a wavelength (nm) while the ordinate indicates the fluorescence intensity. The solvent is methanol and the concentration of the complex is $1 \times 10^{-5}$ M, and it was excited by a light at the wavelength of 361 nm. The measurements were carried out with delay time of 0.1 ms, the measurement time of 0.5 ms, with 100 times of integration.
Figure 9:
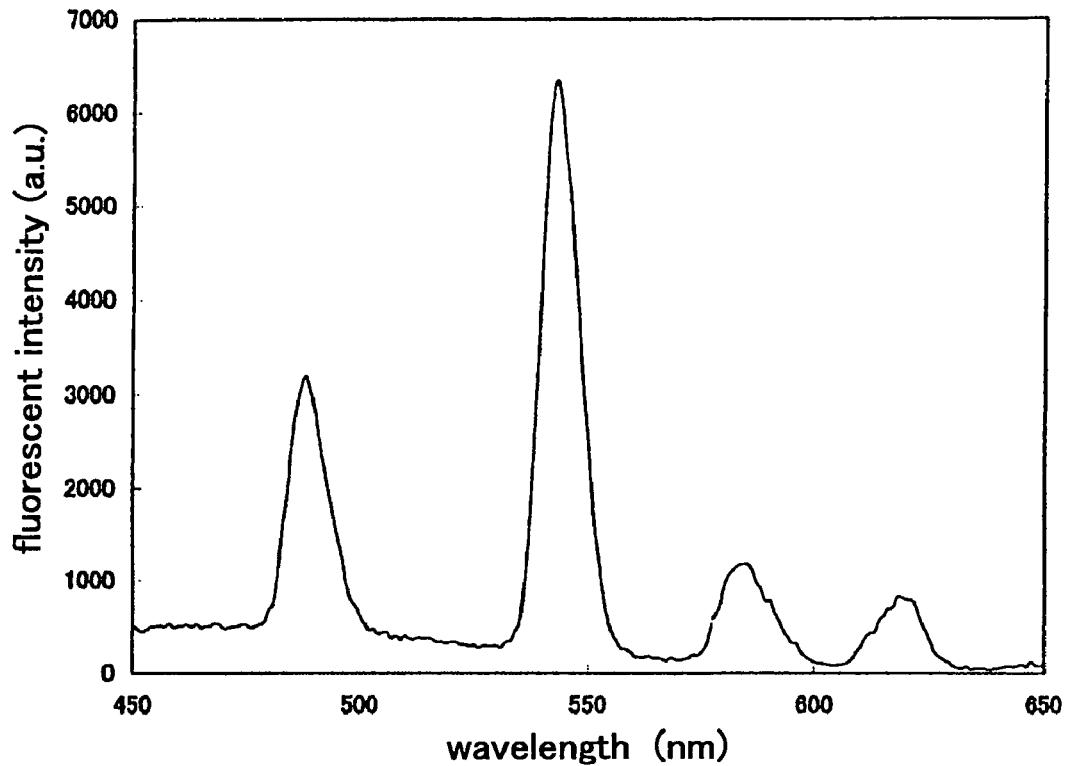
FIG. 9 is a chart showing excitation spectrum measured in a time dissolved mode of amino-BTPDA-Tb compound, which is one of rare-earth fluorescent complexes of the present invention. The abscissa of FIG. 9 indicates a wavelength (nm) while the ordinate indicates the fluorescence intensity. The solvent is methanol and the concentration of the complex is $1 \times 10^{-5}$ M, and the fluorescence at the wavelength of 545 nm was detected. The measurements were carried out with delay time of 0.1 ms, the measurement time of 0.5 ms, with 100 times of integration.
Figure 10:
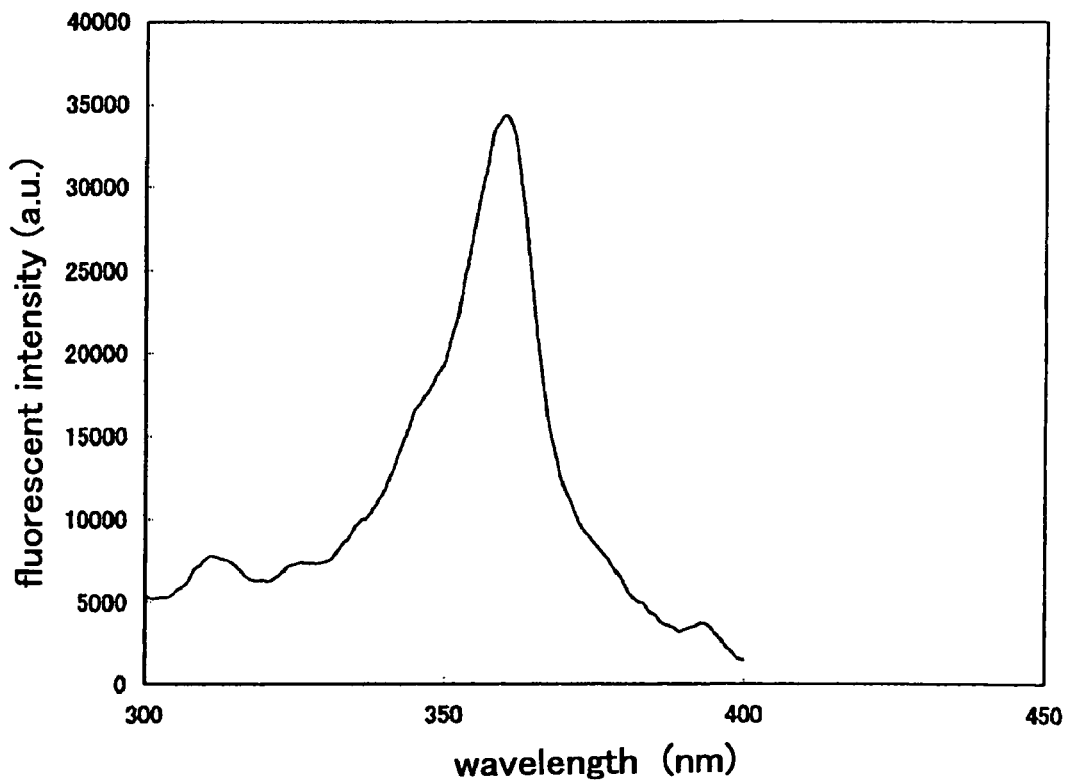
FIG. 10 is a chart showing emission spectrum measured in time dissolved mode of amino-BTPDA-Tb compound, which is one of rare-earth fluorescent complexes of the present invention. The abscissa of FIG. 10 indicates wavelength (nm) while the ordinate indicates fluorescence intensity. The solvent is methanol and the concentration of the complex is $1 \times 10^{-5}$ M, and it was excited by the light at the wavelength of 361 nm. The measurements were carried out with a delay of 0.1 ms, the measurement time of 0.5 ms, with 100 times of integration.

The fluorescent characteristics in a methanol solution with respect to the amino-BTPDA-Eu compound [compound 8-Eu] obtained in Example 7 and the amino-BTPDA-Tb compound [compound 8-Tb] obtained in Example 9 were determined respectively. The excitation spectrum of [compound 8-Eu compound] is shown in FIG. 7, and the emission spectrum thereof is shown in FIG. 8. The excitation spectrum of [compound 8-Tb compound] is shown in FIG. 9, and the emission spectrum thereof is shown in FIG. 10. Each of these rare-earth fluorescent complexes exhibited the same maximum excitation wavelengths of 361 nm, and the emissions specific to the respective central metals (Eu: 614 nm and Tb: 545 nm) were observed.

The resultant data indicated that the rare-earth metal complexes according to the present invention have highly significant absorption characteristics and fluorescent characteristics.

INDUSTRIAL APPLICABILITY

The present invention is to provide a novel rare-earth metal complex which is useful as a fluorescent labeling agent, and a novel compound useful as a ligand thereof. The rare-earth metal complex according to the present invention is capable of binding to a substance to be labeled (such as a biomaterial and a physiologically active substance) via a binding group, stable in an aqueous solution, and has a sufficient fluorescent intensity and a long fluorescent lifetime, moreover, capable of forming a complex with 2 or more rare-earth metals and can produce sufficient fluorescent emission at the wavelength of 340 nm or longer provided by an ordinary laser light source.

Accordingly, the present invention is to provide a fluorescent labeling agent and a material thereof which are useful for a fluorescent immunoassay such as a fluorescent immunoassay and a DNA hybridization assay, particularly for a time resolved fluorescent immunoassay, and therefore it has a high potential for industrial application.

What is claimed is:

1. A compound represented by the following formula (I):

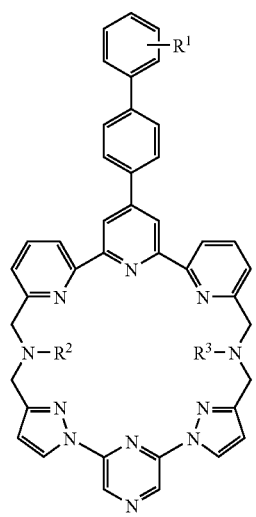

(I)

or a salt thereof, wherein:
   $R^1$ is a nitro group, or an optionally substituted amino group;
   $R^2$ and $R^3$ each independently is a carboxylalkyl group.

2. The compound or the salt thereof according to claim 1, wherein each $R^2$ and $R^3$ in the formula (I) is a carboxymethyl group.

3. The compound or the salt thereof according to claim 1 or 2, where $R^1$ of the formula (I) is a substituted amino group.

4. A rare-earth fluorescent complex comprising a cyclic ligand including 4-biphenyl-2,2':6',2''-terpyridine skeleton and 2,6-bis (3'-aminomethyl-1'-pyrazolyl)pyrazine skeleton bonded thereto; as a ligand.

5. The rare-earth fluorescent complex according to claim 4, wherein the rare-earth fluorescent complex is excitable at a wavelength of 340 nm or longer.

6. The rare-earth fluorescent complex according to claim 4 which is a compound represented by the following formula (II):

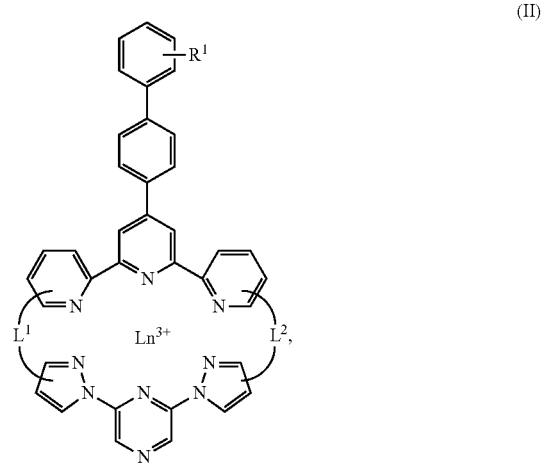

(II)

wherein:
   $R^1$ is a nitro group or an optionally substituted amino group;
   $L^1$ and $L^2$ each independently is a straight or branched chain $C_1$-$C_6$ alkylene group wherein at least one carbon atom is optionally substituted with a nitrogen atom, each of which links both rings and optionally comprises an anionic group to neutralize positive charges of rare-earth ions; and
   Ln is a rare-earth metal.

7. The rare-earth fluorescent complex according to claim 4 which is a compound represented by the following formula (III):

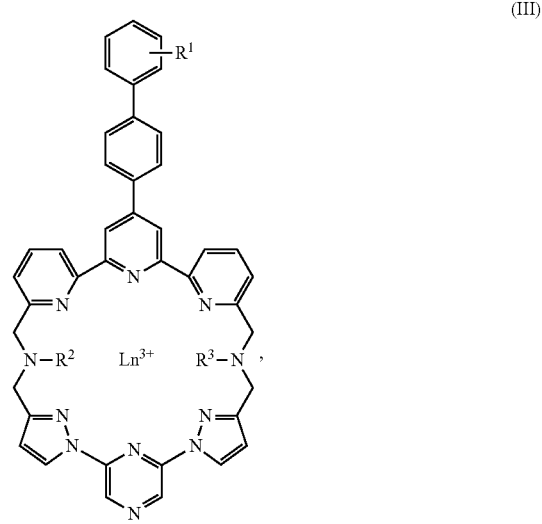

(III)

wherein:
   $R^1$ is a nitro group or an optionally substituted amino group;
   $R^2$ and $R^3$ each independently is a carboxyalkyl group; and
   Ln is a rare-earth metal.

8. The rare-earth fluorescent complex according to claim 6 or 7, where $R^1$ of formula (II) or (III) is a substituted amino group.

9. The rare-earth fluorescent complex according to claim 4, wherein the rare-earth metal comprised therein is terbium or europium.

10. A fluorescent labeling agent to label a substance to be labeled, comprising a rare-earth fluorescent complex according to claim 4.

11. The fluorescent labeling agent according to claim 10, wherein the substance to be labeled is a biomaterial or a physiologically active substance.

12. The fluorescent labeling agent according to claim 11, wherein the biomaterial or the physiologically active substance is an enzyme, a protein, a hormone, a peptide, a nucleic acid, a nucleic acid probe, an oligonucleotide or a drug.

13. A fluorescent labeling method to label a substance to be labeled, wherein the rare-earth fluorescent complex according to claim 4 is bonded to a substance to be labeled via a binding group.

14. The biomaterial or the physiologically active substance labeled with the fluorescent labeling agent according to claim 10.

15. The labeled biomaterial or the physiologically active substance according to claim 14, wherein the biomaterial or the physiologically active substance is an enzyme, a protein, a hormone, a peptide, a nucleic acid, a nucleic acid probe, an oligonucleotide or a drug.

16. A fluorescent assay comprising binding the fluorescent labeling agent according to claim 10 to the substance to be labeled via the binding group, thereby labeling the substance to be labeled, and measuring fluorescence of the fluorescent labeling agent.

17. The fluorescent assay according to claim 16, wherein the fluorescent assay is a time-resolved fluorescence assay.

18. The fluorescent assay according to claim 17, wherein the time-resolved fluorescence assay is a time-resolved fluorescent immunoassay, a time-resolved fluorescent DNA hybridization assay, a time-resolved fluorescent microscopic imaging or time-resolved fluorescent chromatography.

19. A kit for fluorescent assay comprising the fluorescent labeling agent according to claim 10.

20. The fluorescent labeling agent according to claim 12, wherein the drug comprises an antibiotic.

21. The, labeled biomaterial or the physiologically active substance according to claim 15, wherein the drug comprises an antibiotic.

* * * * *